(12) United States Patent
Krivoruchko

(10) Patent No.: US 11,832,828 B2
(45) Date of Patent: Dec. 5, 2023

(54) LEFT ATRIAL APPENDAGE OCCLUSION DEVICE

(71) Applicant: Medtronic, Inc., Minneapolis, MN (US)

(72) Inventor: Michael Krivoruchko, Forestville, CA (US)

(73) Assignee: Medtronic, Inc., Minneapolis, MN (US)

( * ) Notice: Subject to any disclaimer, the term of this patent is extended or adjusted under 35 U.S.C. 154(b) by 142 days.

(21) Appl. No.: 16/879,610

(22) Filed: May 20, 2020

(65) Prior Publication Data

US 2020/0367903 A1  Nov. 26, 2020

Related U.S. Application Data

(60) Provisional application No. 62/852,952, filed on May 24, 2019.

(51) Int. Cl.
*A61B 17/12* (2006.01)
*A61M 25/10* (2013.01)
*A61B 17/00* (2006.01)

(52) U.S. Cl.
CPC .. *A61B 17/12122* (2013.01); *A61B 17/12145* (2013.01); *A61B 17/12172* (2013.01);
(Continued)

(58) Field of Classification Search
CPC ........ A61B 17/12122; A61B 17/12145; A61B 17/12172; A61B 17/12168; A61B 17/1215; A61B 17/12031; A61B 17/12177; A61B 17/0057; A61B 17/12099; A61B 17/12036; A61B 17/1204; A61B 17/12045; A61B 2017/00004; A61B 2017/00867; A61B 2017/12054; A61B 2017/12095; A61B 2017/00557; A61B 2017/00986; A61B 2017/00632; A61B 2017/00575; A61B 2017/00243; A61B 2017/00597; A61B 17/12022; A61B 17/12109; A61B 17/12113; A61F 2/0009; A61F 2/01; A61F 2/0105; A61F 2/82; A61F 2/011;
(Continued)

(56) References Cited

U.S. PATENT DOCUMENTS 8,690,911 B2 * 4/2014 Miles ................. A61B 17/1215
606/213
2002/0049493 A1 * 4/2002 Jang ........................ A61F 2/915
623/1.16

(Continued)

FOREIGN PATENT DOCUMENTS

CN 112826561 A * 5/2021 ....... A61B 17/12122
EP 2399524 A1 * 12/2011 ......... A61B 17/0057
(Continued)

OTHER PUBLICATIONS

International Search Report and Written Opinion, International Application No. PCT/US2020/033916, dated Sep. 18, 2020. 22 pages.

*Primary Examiner* — Katherine M Shi
(74) *Attorney, Agent, or Firm* — Medler Ferro Woodhouse Mills PLLC

(57) ABSTRACT

An occlusion device for the left atrial appendage is plastically deformable and biodegradable.

9 Claims, 11 Drawing Sheets

(52) U.S. Cl.
CPC ... *A61M 25/10* (2013.01); *A61B 2017/00004* (2013.01); *A61B 2017/00867* (2013.01); *A61B 2017/12054* (2013.01); *A61B 2017/12095* (2013.01)

(58) Field of Classification Search
CPC .......... A61F 2/02; A61F 2/012; A61F 2/2002; A61F 2/016; A61F 2/015; A61F 2002/018; A61F 2/90; A61F 2230/0071; A61F 2002/016; A61F 2230/0006; A61F 2250/0039; A61F 2/2418; A61F 2/07; A61F 2/24; A61F 2/86; A61M 25/10
USPC .......................................................... 606/200
See application file for complete search history.

(56) References Cited

U.S. PATENT DOCUMENTS

| | | | | |
|---|---|---|---|---|
| 2004/0030335 | A1* | 2/2004 | Zenati | A61B 17/12013 606/51 |
| 2005/0060042 | A1* | 3/2005 | Phan | A61B 17/064 623/1.42 |
| 2007/0112380 | A1* | 5/2007 | Figulla | A61B 17/12122 606/213 |
| 2009/0312789 | A1* | 12/2009 | Kassab | A61B 17/0057 606/213 |
| 2011/0022079 | A1* | 1/2011 | Miles | A61B 17/0401 606/213 |
| 2011/0082495 | A1* | 4/2011 | Ruiz | A61B 17/0057 606/213 |
| 2011/0282428 | A1 | 11/2011 | Meyer et al. | |
| 2012/0172927 | A1* | 7/2012 | Campbell | A61B 17/12122 606/213 |
| 2012/0271337 | A1* | 10/2012 | Figulla | A61B 17/12122 606/191 |
| 2013/0138138 | A1* | 5/2013 | Clark | A61B 17/12022 606/200 |
| 2014/0142617 | A1* | 5/2014 | Larsen | A61B 17/12031 606/213 |
| 2014/0277070 | A1* | 9/2014 | Otero | A61B 17/12186 606/194 |
| 2015/0039023 | A1* | 2/2015 | de Canniere | A61B 17/12122 606/215 |
| 2018/0132861 | A1* | 5/2018 | Degen | A61B 17/12122 |
| 2018/0235640 | A1* | 8/2018 | Slaughter | A61B 17/064 |
| 2019/0110880 | A1 | 4/2019 | Fox et al. | |
| 2019/0183512 | A1* | 6/2019 | Subramaniam | A61B 17/12027 |
| 2020/0229924 | A1* | 7/2020 | Chan | A61B 17/12109 |
| 2021/0137507 | A1* | 5/2021 | Keren | A61B 17/12122 |

FOREIGN PATENT DOCUMENTS

| | | | | |
|---|---|---|---|---|
| KR | 20150042824 A | * | 4/2015 | ............ A61B 17/11 |
| WO | WO-2014210263 A1 | * | 12/2014 | ......... A61B 17/0057 |

* cited by examiner

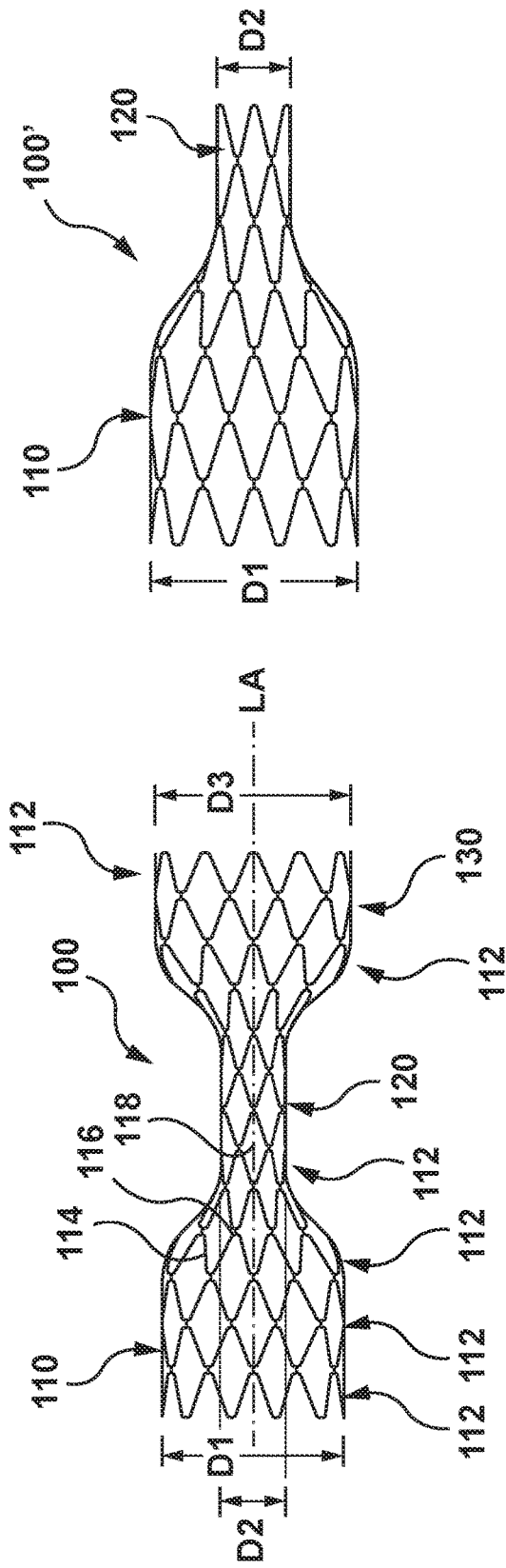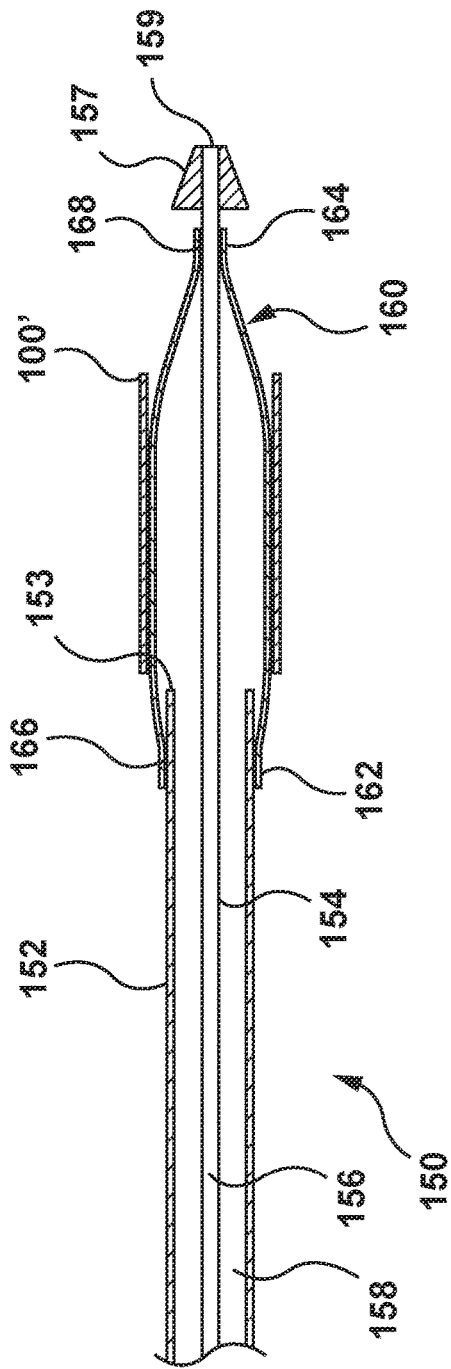
FIG. 2
FIG. 3
FIG. 4

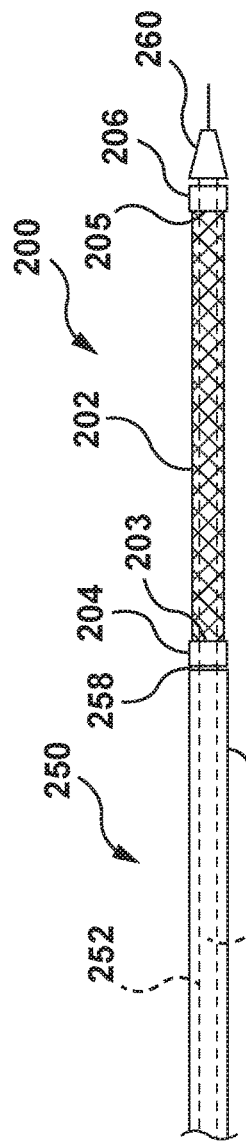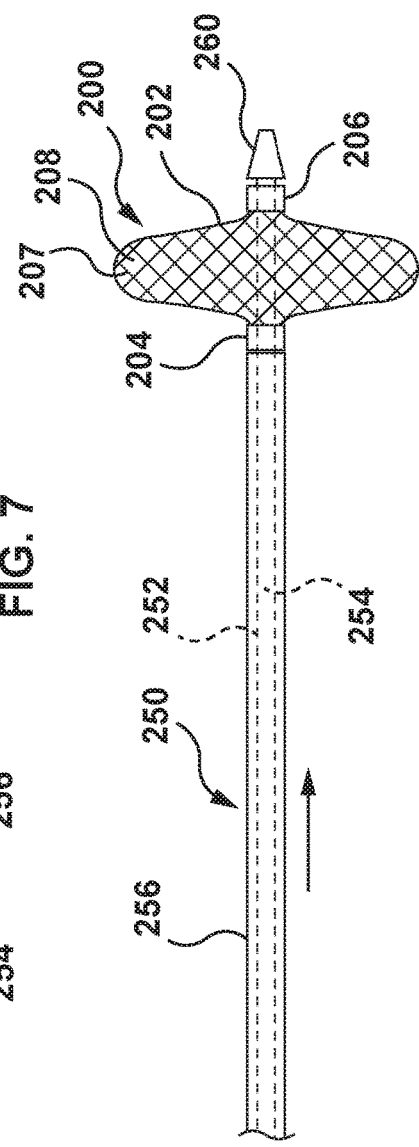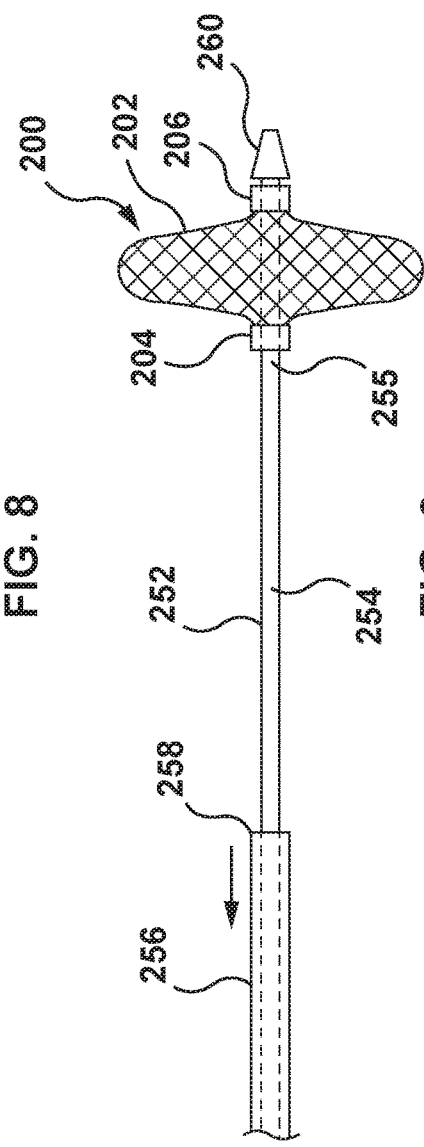

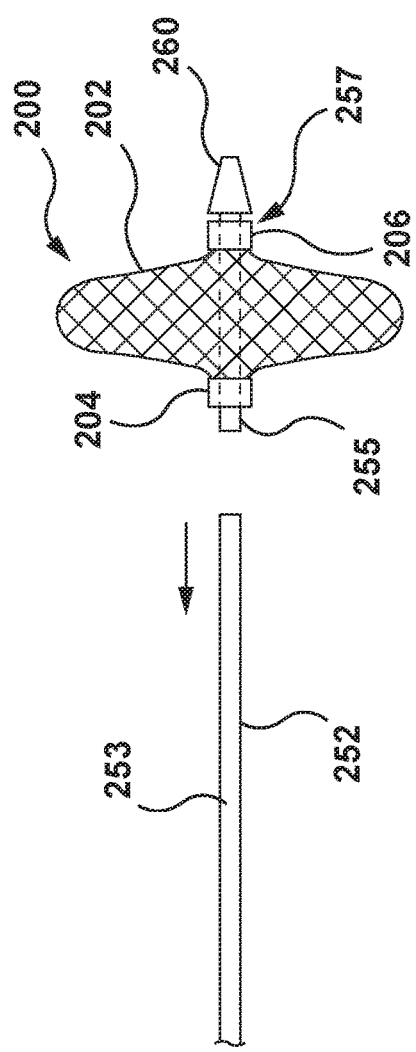
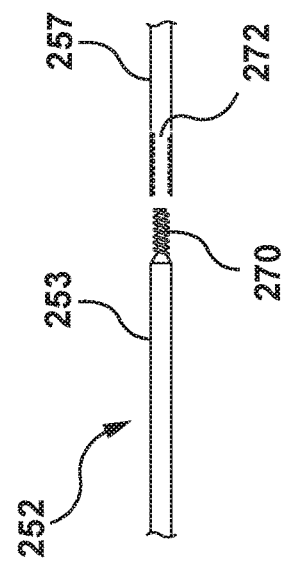
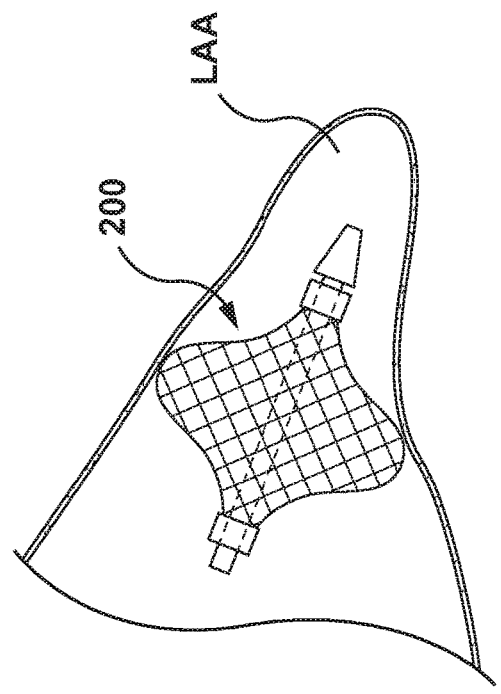
FIG. 10
FIG. 12
FIG. 11

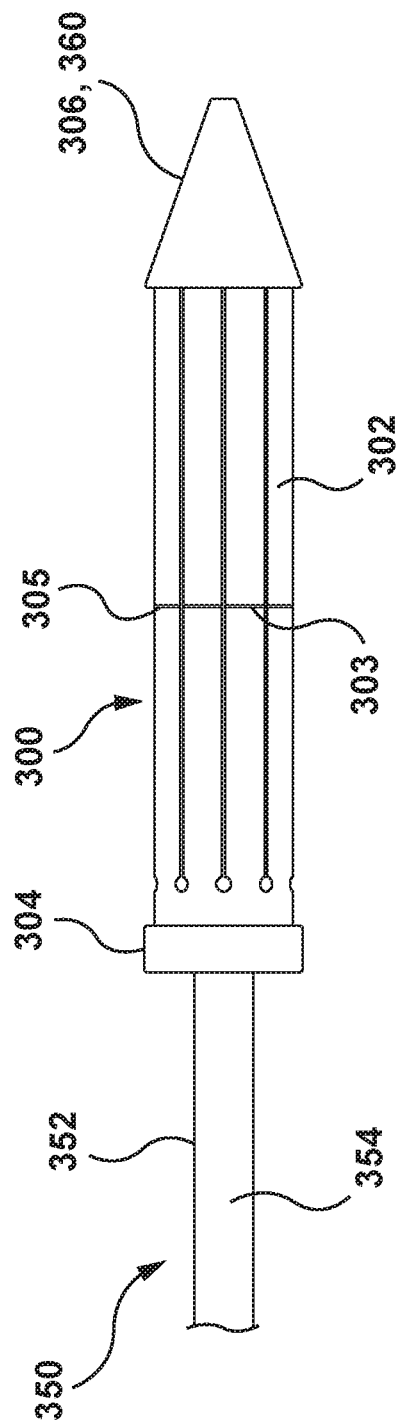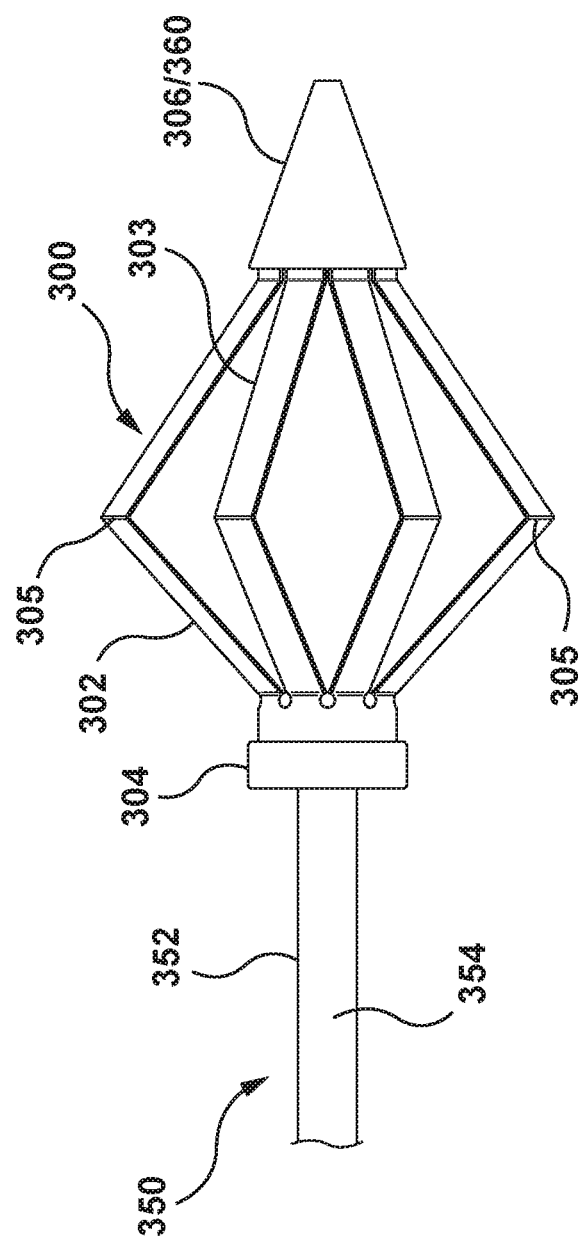

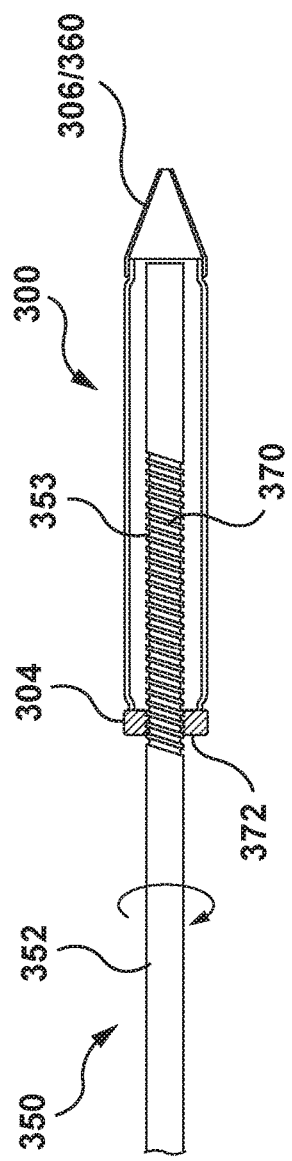
FIG. 15
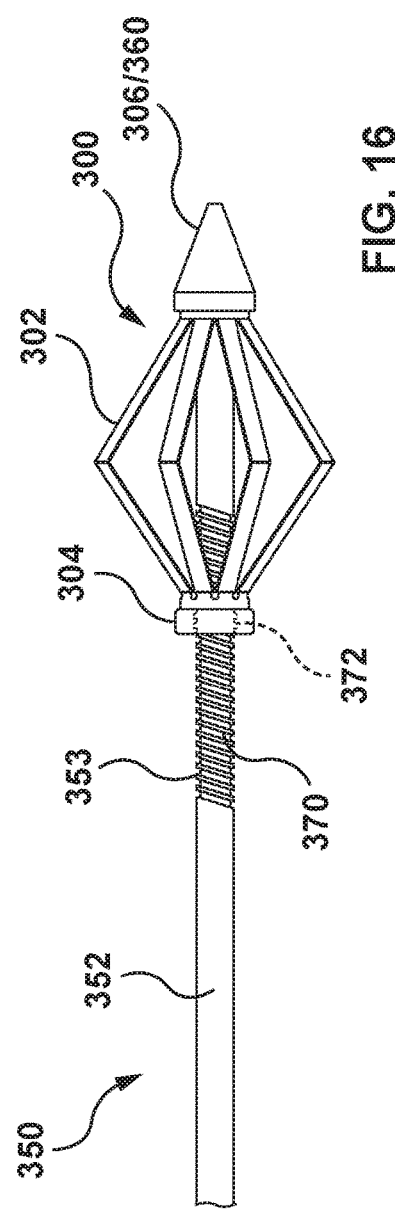
FIG. 16
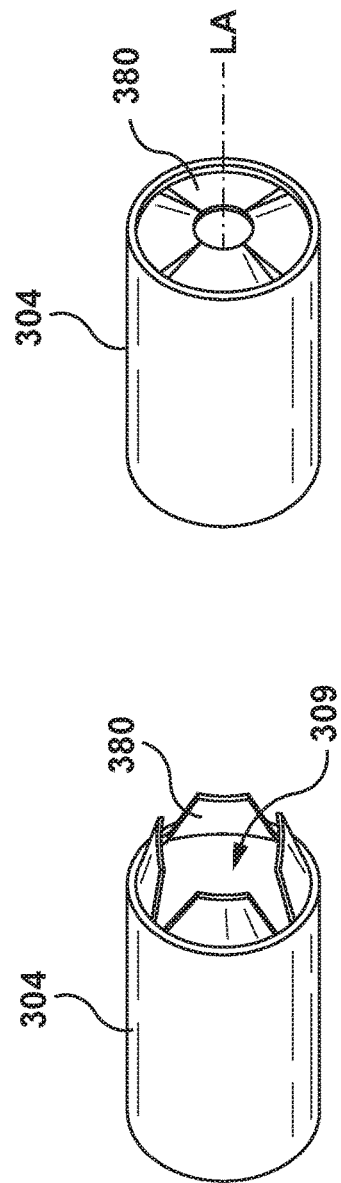
FIG. 17
FIG. 18

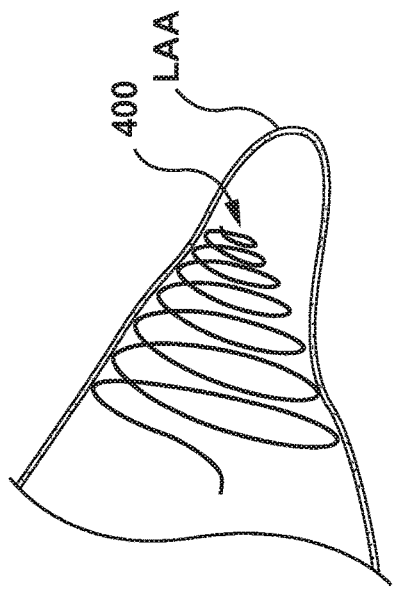
FIG. 22
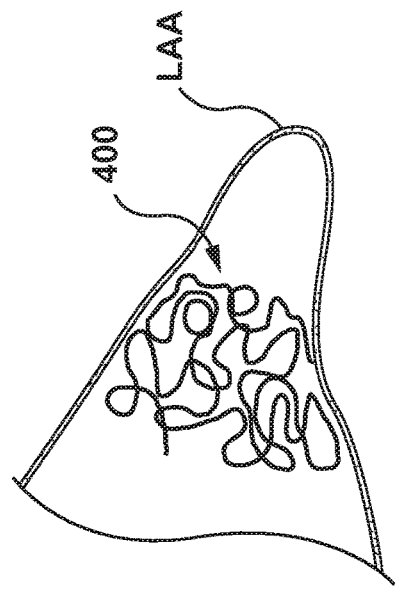
FIG. 24
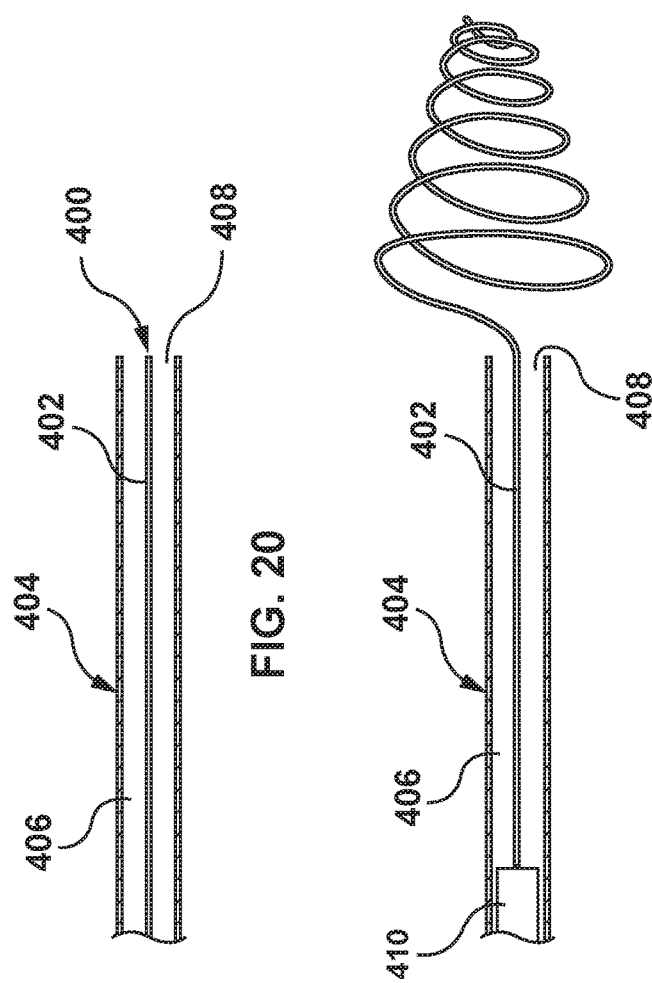
FIG. 20
FIG. 21
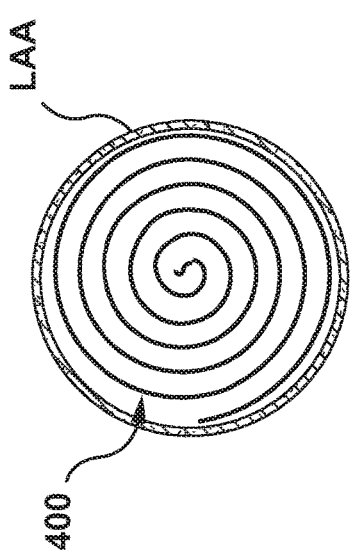
FIG. 23

LEFT ATRIAL APPENDAGE OCCLUSION DEVICE

CROSS-REFERENCE TO RELATED APPLICATIONS

The present application claims the benefit of the filing date of U.S. provisional application No. 62/852,952, filed May 24, 2019, the contents of which are incorporated by reference herein in their entirety.

FIELD OF THE INVENTION

The present invention relates to device, systems and methods for occluding a left atrial appendage of a heart.

BACKGROUND OF THE INVENTION

The human heart is a four chambered, muscular organ that provides blood circulation through the body during a cardiac cycle. Referring to FIG. 1, the four main chambers include the right atrium RA and the right ventricle RV which supplies the pulmonary circulation, and the left atrium LA and the left ventricle LV which supplies oxygenated blood received from the lungs to the remaining body. The heart also includes a left atrial appendage LAA, which is a small, ear-shaped sac in the muscle wall of the left atrium LA. In normal hearts, when the heart contracts, the blood in the left atrium LA and the left atrial appendage LAA is squeezed out of the left atrium LA and into the left ventricle LV.

When a patient has atrial fibrillation, the electrical impulses that control the heartbeat do not travel in an orderly fashion through the heart. Instead, many impulses begin at the same time and spread through the atria. The fast and chaotic impulses do not give the atria time to contract and/or effectively squeeze blood into the ventricles. Because the left atrial appendage LAA is a small sac or pouch, blood collects there and can form clots in the left atrial appendage LAA and atria. When blood clots are pumped out of the heart, they can cause a stroke. People with atrial fibrillation are 5 to 7 times more likely to have a stroke than the general population. Further, studies have shown that among patients who do not have heart valve disease, the majority of blood clots that occur in the left atrium LA start in the left atrial appendage LAA.

Treatment for patients with atrial fibrillation to reduce the risk of stroke include taking a blood thinner, such as warfarin. However, in some cases, a blood thinner is not tolerated by the patient or increases other risks. Thus, in some cases, it may be desirable to exclude or occlude the LAA such that clots do not form in the LAA, and if they do, cannot escape the LAA.

Accordingly, there is a need for catheter-based occlusion systems for occluding or excluding the LAA.

BRIEF SUMMARY OF THE INVENTION

Embodiments hereof relate to an occlusion device for occluding a left atrial appendage. In embodiments, the occlusion device includes a first portion and a second portion attached to the first portion. The occlusion device is plastically deformable from a radially compressed configuration to a radially expanded configuration. In the radially expanded configuration, the first portion has a larger cross-sectional profile than the second portion. In some embodiments, the occlusion device is biodegradable.

Embodiments hereof also relate to an occlusion device for occluding a left atrial appendage including a braided mesh plastically deformable from a radially compressed configuration to a radially expanded configuration, wherein the braided mesh is biodegradable. In embodiments, the occlusion device further includes a first collar and a second collar, wherein a first longitudinal end of the braided mesh is coupled to the first collar and a second longitudinal end of the braided mesh is coupled to the second collar.

Embodiments hereof also relate to an occlusion device for a left atrial appendage including a first collar, a second collar, and a plurality of struts extending between the first collar and the second collar, each of the plurality of struts having a first end coupled to the first collar, a second end coupled to the second collar, and a middle portion extending between the first end and the second end. In a radially compressed configuration, the first collar and the second collar are disposed a first distance from each other and the plurality of struts are disposed circumferentially around a central longitudinal axis. In a radially expanded configuration, the first collar and the second collar are disposed a second distance from each other, the second distance being smaller than the first distance. In the radially expanded configuration, the middle portion of each of the plurality of struts is bent radially outwardly. In some embodiments, the middle portion of each of the plurality of struts includes a hinge for preferential bending to the radially expanded configuration. In some embodiments, the occlusion device is biodegradable. In some embodiments, the plurality of struts are plastically deformable from the radially compressed configuration to the radially expanded configuration.

Embodiments hereof also relate to an occlusion device for a left atrial appendage including a shape memory, biodegradable wire, the wire including a straightened configuration in which the wire is substantially straight and a deployed configuration in which the wire is configured to occlude a left atrial appendage. In some embodiments, the wire is shape set to the deployed configuration. In some embodiments, the wire in the deployed configuration is a spiral shape. In some embodiments, the wire in the deployed configuration is a coil shape.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 2 is a schematic side view illustration of an occlusion device according to an embodiment hereof.

FIG. 3 is a schematic sectional illustration of an occlusion device according to another embodiment hereof.

FIG. 4 is a schematic sectional illustration of a distal end of a balloon catheter with the occlusion device of FIG. 3 mounted thereon with the balloon of the balloon catheter uninflated and the occlusion device in a radially compressed configuration.

3 mounted thereon with the balloon inflated to radially expand the occlusion device to a radially expanded configuration.

Figure 6:
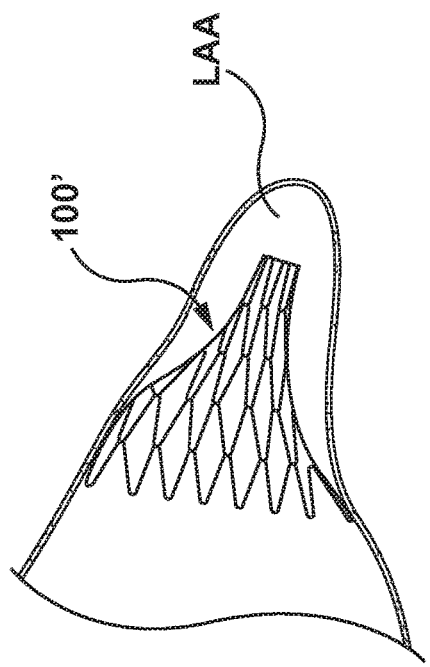

FIG. 6 is a schematic illustration of the occlusion device of FIG. 3 deployed within a left atrial appendage.

FIG. 7 is a schematic illustration of an occlusion device according to another embodiment hereof mounted on a catheter according to another embodiment hereof, with the occlusion device in a radially compressed configuration.

FIG. 8 is a schematic illustration of the catheter and occlusion device of FIG. 7 with the occlusion device in a radially expanded configuration.

FIG. 9 is a schematic illustration of the catheter and occlusion device of FIG. 7 with the occlusion device in a radially expanded configuration and an outer shaft retracted.

FIG. 10 is a schematic illustration of the catheter and occlusion device of FIG. 7 with the occlusion device in a radially expanded configuration and a proximal portion of an inner shaft disconnected from a distal portion of the inner shaft.

FIG. 11 is a schematic illustration of the occlusion device of FIG. 7 deployed within a left atrial appendage.

FIG. 12 is a schematic illustration of an embodiment of an embodiment of the inner shaft of the catheter of FIG. 7.

FIG. 13 is a schematic illustration of an occlusion device according to another embodiment hereof mounted on a catheter according to another embodiment hereof, with the occlusion device in a radially compressed configuration.

FIG. 14 is a schematic illustration of the catheter and occlusion device of FIG. 13 with the occlusion device in a radially expanded configuration.

FIG. 15 is a schematic sectional illustration of the catheter and occlusion device of FIG. 13 showing an embodiment of a shaft of the catheter with the occlusion device in the radially compressed configuration.

FIG. 16 is a schematic sectional illustration of the catheter and occlusion device of FIG. 15 with the shaft moved to radially expand the occlusion device FIG. 17 is a schematic illustration of an embodiment of a collar of the occlusion device of FIG. 13.

FIG. 18 is a schematic illustration of the collar of FIG. 17 with flaps thereof covering an opening of the collar.

Figure 19:
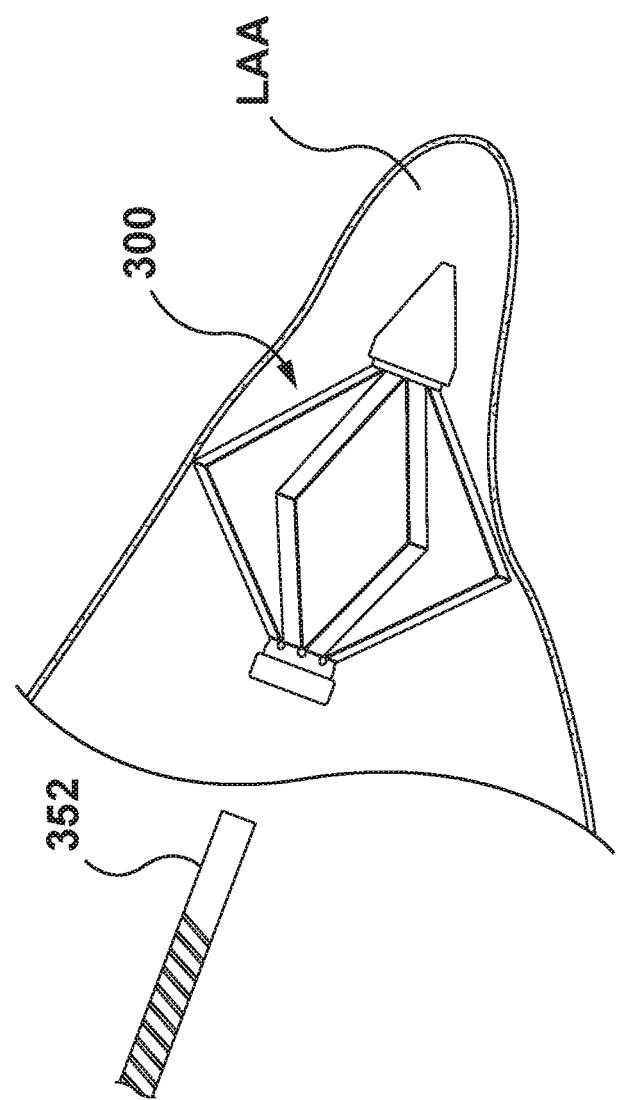

FIG. 19 is a schematic illustration of the occlusion device of FIG. 13 deployed within a left atrial appendage.

FIG. 20 is a schematic illustration of an occlusion device according to another embodiment hereof disposed within a catheter in a straightened configuration.

FIG. 21 is a schematic illustration of the occlusion device of FIG. 21 partially released from the catheter and in a partially deployed configuration.

FIG. 22 is a schematic illustration of the occlusion device of FIG. 20 deployed within a left atrial appendage.

FIG. 23 is schematic plan view from the left atrium of the occlusion device of FIG. 20 deployed within a left atrial appendage.

FIG. 24 is a schematic illustration of the occlusion device of FIG. 20 deployed within a left atrial appendage, wherein the occlusion device has a different pre-set shape.

Figure 25:
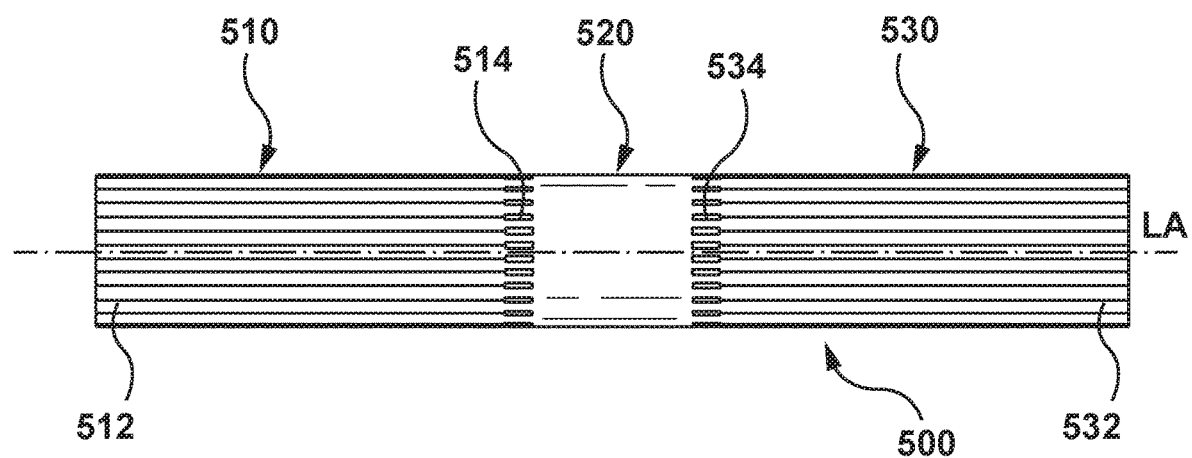

FIG. 25 is a schematic illustration of an occlusion device in a radially compressed configuration according to another embodiment hereof.

Figure 26:
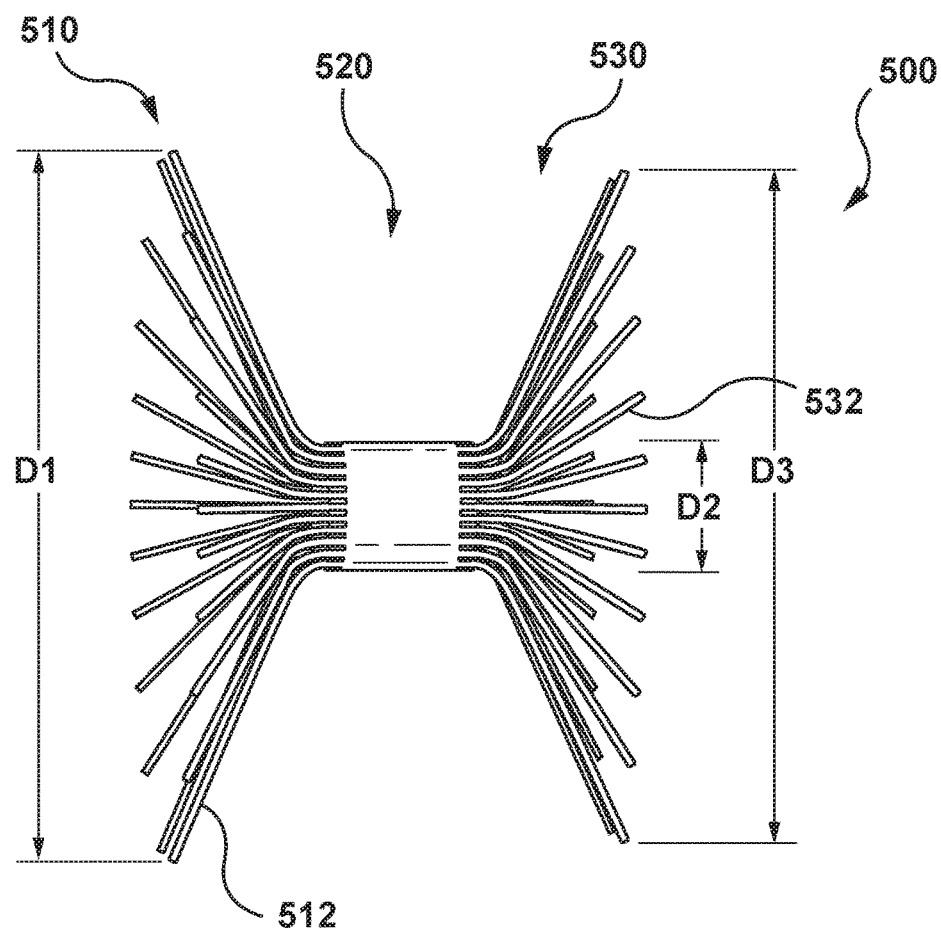

FIG. 26 is a schematic illustration of the occlusion device of FIG. 25 in a radially expanded configuration.

Figure 27:
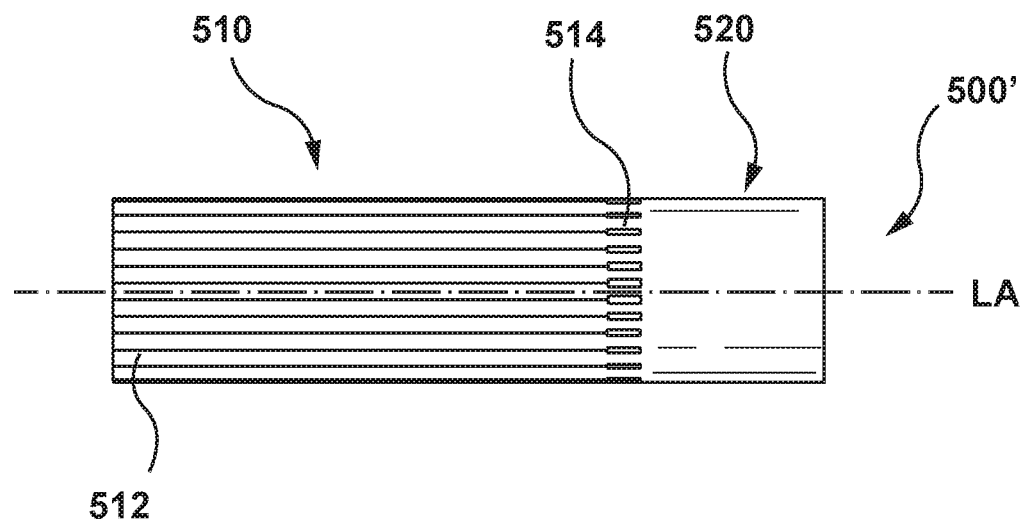

FIG. 27 is a schematic illustration of an occlusion device in a radially compressed configuration according to another embodiment hereof.

Figure 28:
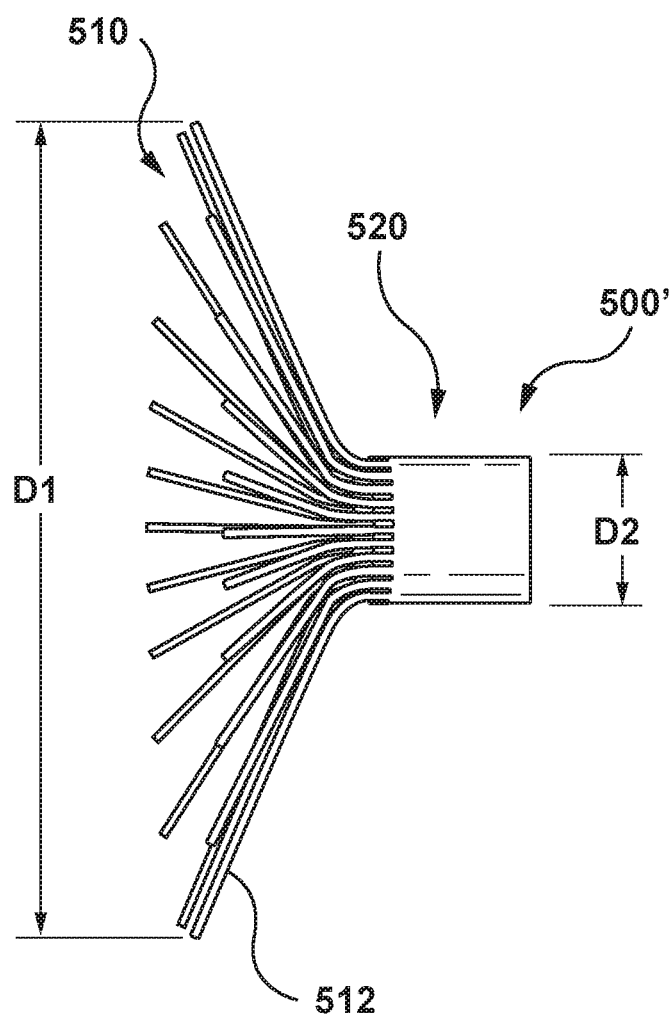

FIG. 28 is a schematic illustration of the occlusion device of FIG. 27 in a radially expanded configuration.

DETAILED DESCRIPTION OF THE INVENTION

Specific embodiments of the present invention are now described with reference to the figures, wherein like reference numbers indicate identical or functionally similar elements. The terms "distal" and "proximal", when used in the following description to refer to a catheter and/or other system components hereof are with respect to a position or direction relative to the treating clinician. Thus, "distal" and "distally" refer to positions distant from or in a direction away from the treating clinician, and the terms "proximal" and "proximally" refer to positions near or in a direction toward the treating clinician. The terms "distal" and "proximal", when used in the following description to refer to a native vessel, native valve, or a device to be implanted into a native vessel or native valve, are with reference to the direction of blood flow. Thus, "distal" and "distally" refer to positions in a downstream direction with respect to the direction of blood flow and the terms "proximal" and "proximally" refer to positions in an upstream direction with respect to the direction of blood flow.

The following detailed description is merely exemplary in nature and is not intended to limit the invention or the application and uses of the invention. There is no intention to be bound by any expressed or implied theory presented in the preceding technical field, background, brief summary or the following detailed description.

Figure 1:
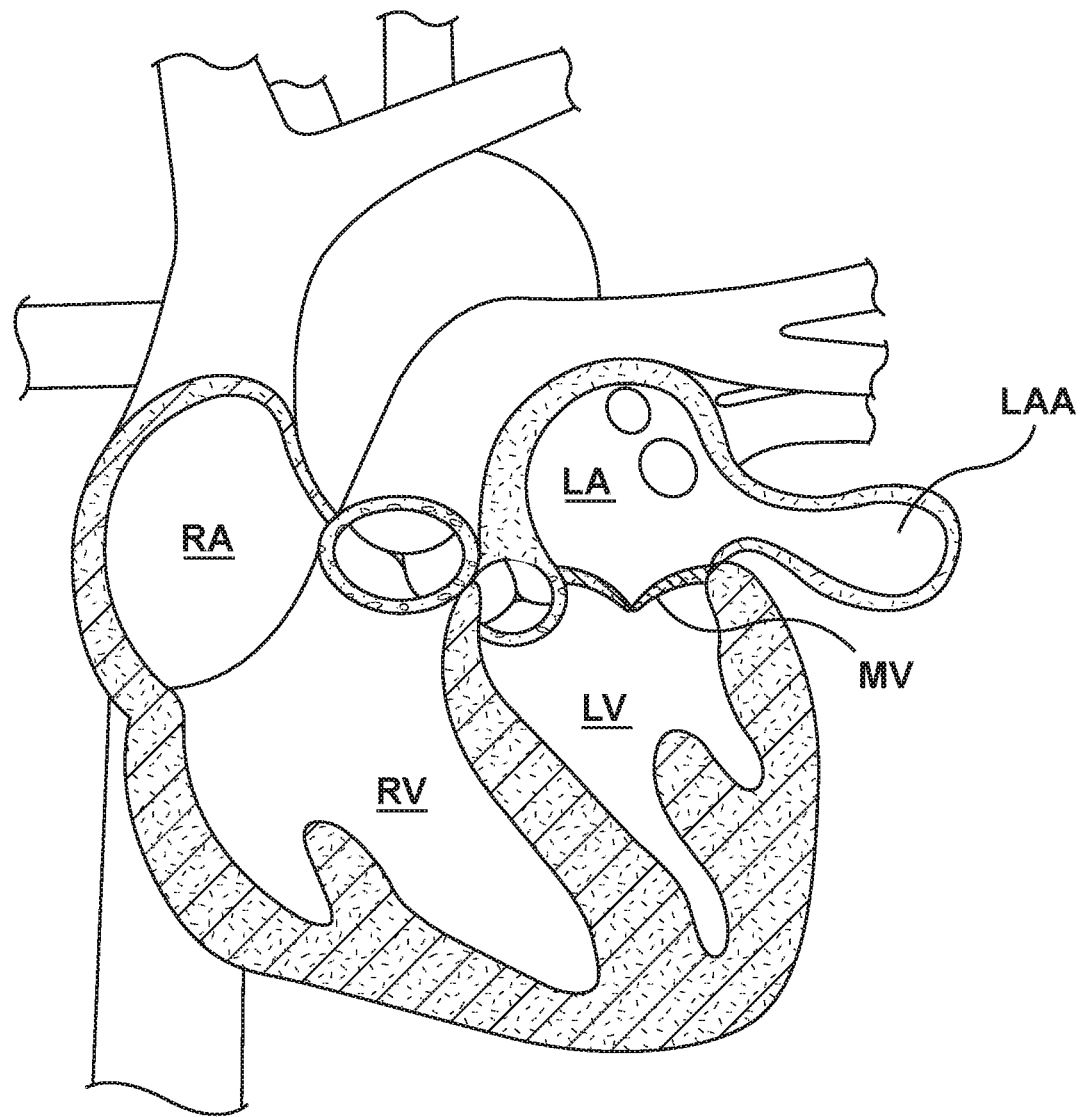
FIG. 1 is a schematic sectional illustration of a mammalian heart.

FIG. 1 is a schematic sectional illustration of a human heart HE that depicts the four heart chambers (right atrium RA, right ventricle RV, left atrium LA, left ventricle LV) and a left atrial appendage LAA. As noted above, patients with non-valvular atrial fibrillation are at risk for blood clots forming in the left atrial appendage LAA and being released therefrom, possibly causing a stroke.

Figure 5:
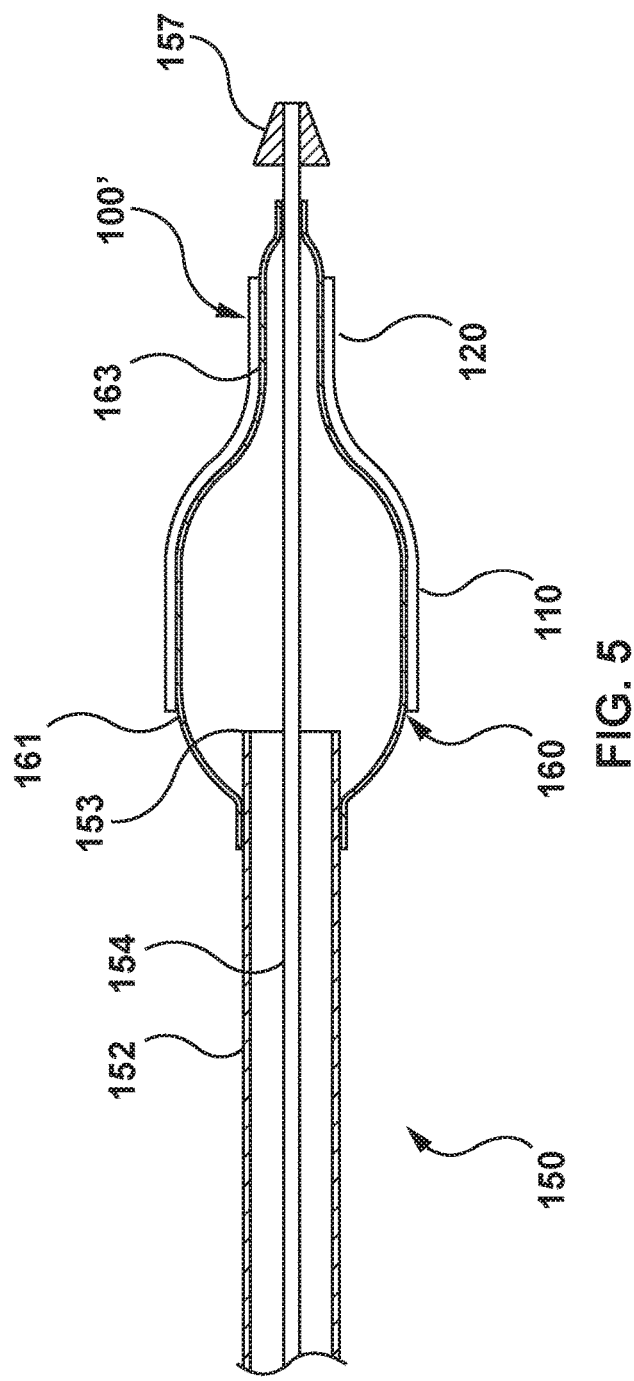
FIG. 5 is a side view illustration the distal end of the balloon catheter of FIG. 4 with the occlusion device of FIG.

FIGS. 2 and 3 show similar embodiments of occlusion devices 100, 100' in a radially expanded configuration for use in occluding the left atrial appendage. FIGS. 4 and 5 show a balloon catheter with the occlusion device 100' of FIG. 3 mounted thereon, but the balloon catheter could also be used for the occlusion device 100 of FIG. 2. FIG. 6 shows the occlusion device 100' of FIG. 3 disposed in a left atrial appendage LAA.

Referring back to FIG. 2, the occlusion device 100 includes a first portion 110, a second portion 120, and a third portion 130. In the embodiment of FIG. 2, the second portion 120 is disposed between the first portion 110 and the third portion 130, and connects the first portion 110 to the third portion 130. Further, the second portion 120 is reduced in diameter or cross-sectional profile when the occlusion device 100 is in a radially expanded configuration. Accordingly, in the radially expanded configuration, the first portion 110 has a first cross-sectional profile or diameter D1, the second portion 120 has a second cross-sectional profile or diameter D2, and the first third portion 130 has a third cross-sectional profile or diameter D3. The second diameter D2 is smaller than the first diameter D1 and the third diameter D3. The third diameter D3, in some embodiments, may be equal to the first diameter D1. In other embodiments, the third diameter D3 may be larger or smaller than the first diameter D1.

In the embodiment of FIG. 2, each portion 110, 120, 130 is formed of series of elements or rings 112 disposed adjacent to each other around a central longitudinal axis LA.

Each ring 112 includes struts 114 and bends 116, with adjacent struts 112 being connected to each other by a respective bend 116. In some embodiments, adjacent rings 112 are connected to each other by connectors 118. The particular details regarding the parts of the occlusion device 100 may be varied. For example, and not by way of limitation, instead of connected rings 112, the occlusion device 100 may be formed of a waveform including struts and bends, and then the waveform may be helically wrapped to form the occlusion device 100. In some embodiments, a single waveform may form all of the first, second, and third portions 110, 120, and 130. In other embodiments, individual waveforms may be used for each of the first, second, and third portions, 110, 120, 130, and the individual waveforms may be connected to form the occlusion device 100. In other embodiments, the occlusion device 100 may be formed of a braided wire.

FIG. 3 shows an occlusion device 100' that is similar to the occlusion device 100 except that the occlusion device 100' includes only the first portion 110 and the second portion 120, wherein in the radially expanded configuration, the second portion 120 has a reduced second cross-sectional profile D2 as compared to a first cross-sectional profile or diameter D1 of the first section 110. The first and second sections 110 and 120 of the occlusion device 100' may be made in the same manner described above with respect to the occlusion device 100, including the alternatives described.

In each of the occlusion devices 100, 100', it is desirable to make the second diameter D2 as small as possible. As described in more detail below, when delivering and deploying the occlusion device 100 or the occlusion device 100' using a balloon catheter, the second diameter D2 need only be large enough such that the balloon catheter may be withdrawn from the radially expanded occlusion device 100 or 100' after the balloon of the balloon catheter has been deflated.

The occlusion devices 100, 100' may be formed of plastically deformable materials such that the occlusion devices 100, 100' are plastically deformable. Such devices may also be referred to as balloon or mechanically expandable. Further, the occlusion devices 100, 100' may be biodegradable or bioerodible such that the occlusion devices degrade/erode over time after being deployed within the left atrial appendage LAA of a human heart HE. For example, and not by way of limitation, plastically deformable and biodegradable/bioerodible materials suitable for use for the occlusion devices 100. 100' include biodegradable metals or metal alloys such as alloys whose main component (largest amount by weight) is selected from the group consisting of magnesium, iron, zinc or tungsten. Other plastically deformable and biodegradable/bioerodible materials include biodegradable polymers such as, but not limited to, poly L-lactic acid (PLLA), poly lactic acid (PLA), polyglycolic acid (PGA), poly glycolide-co-L-lactide acid (PGLA), polydioxanone (PDO), poly glycolide-co-caprolactone (PGCL), and similar materials.

FIGS. 4 and 5 show a distal portion of a balloon catheter 150 for delivering and deploying the occlusion device 100 or the occlusion device 100'. In the embodiment shown in FIGS. 4 and 5, the occlusion device 100' is shown mounted on the balloon catheter 150, but that is not limiting, and the occlusion device 100, or the occlusion devices described below, may be delivered and deployed using the balloon catheter 150.

The balloon catheter 150 includes an outer shaft 152, an inner shaft 154 disposed within the outer shaft 152, and a balloon 160 attached to the outer and inner shafts 152, 154, as described below. The inner shaft 154 defines a guidewire lumen 156 that extends to a distal end of the inner shaft 154. The guidewire lumen 156 may extend to a proximal end (not shown) of the inner shaft 154 or may terminate distal of the proximal end of the inner shaft 154 in a rapid exchange configuration, known to those skilled in the art. A distal tip 157 is coupled to a distal portion of the inner shaft 154. A tip lumen 159 of the distal tip 157 is in communication with the guidewire lumen 156 such that a guidewire may extend through the guidewire lumen 156 and the tip lumen 159 to enable the catheter 150 to be guided over the guidewire. An annular inflation lumen 158 is defined between an inner surface of the outer shaft 152 and an outer surface of the inner shaft 154. In other embodiments, rather than an annular inflation lumen, a separate shaft with an inflation lumen may be disposed adjacent the inner shaft 154, or a dual lumen shaft may be used as the inner shaft. A proximal portion of the catheter 150 (not shown) may include features such as a handle or luer, an inflation source fluidly coupled to the inflation lumen 158, and other features known to those skilled in the art.

The balloon 160 includes a proximal neck 162 and a distal neck 164. The proximal neck 162 of the balloon 160 is attached to a distal portion of the outer shaft 152 at a connection 166. The distal neck 164 of the balloon 160 is attached to a distal portion of the inner shaft 154 at a connection 168. The connections 166, 168 may be adhesive or other mechanical connections, for example. An open distal end 153 of the outer shaft 152 extends into an interior of the balloon 160 such that inflation fluid from the inflation lumen 158 flows into the interior of the balloon 160 to inflate the balloon 160, as known to those skilled in the art.

FIG. 5 shows the catheter 150 with the balloon 160 inflated to radially expand the occlusion device 100' to the radially expanded configuration. Radially expanding the occlusion device 100' causes the occlusion device 100' to plastically deform such that after deflation of the balloon 160, the occlusion device 100' remains in the radially expanded configuration. As shown in FIG. 5, the first portion 110 of the occlusion device 100' is expanded to a larger cross-sectional profile or diameter than the second portion 120. This may be accomplished, for example and not by way of limitation, by the balloon 160 including a first portion 161 being configured to radially expand to a larger diameter than a second portion 163 of the balloon 160. In another embodiment, rather than a single balloon 160, two balloons may be provided adjacent to each other, with the first portion 110 of the occlusion device 100' disposed over the first balloon and the second portion 120 of the occlusion device disposed over the second balloon. The first and second balloons are configured to radially expand to different diameters, such that the first and second portions 110, 120 of the occlusion device 100' radially expand to different diameters. In such an embodiment, the catheter may include separate inflation lumens for each of the balloons, or an inflation lumen that extends to both balloons with lateral openings into each of the balloons. In another embodiment, the occlusion device 100' is designed such that the first portion 110 radially expands to the first diameter D1, while second portion 120 radially expands to the second diameter D2 using a balloon with uniform expansion. For example, and not by way of limitation, the struts 114 and/or bends 116 of the second portion 120 may be thicker than the struts 114 and/or bends 116 of the first portion 110 such that the second portion 120 resists radial expansion to a greater degree than the first portion 110. Other ways to make the second portion more resistant to radial expansion may also be utilized. The descriptions above regarding the balloon catheter 150 and the balloon 160 apply to the balloon catheter 150 used with the occlusion device 100 except that the balloon 160 (or balloons) may include a third portion configured to expand the third portion 130 of the occlusion device 100 to the third diameter D3, or the third portion 130 of the occlusion device 100 will be configured to expand to the third diameter D3 with a uniform balloon.

With the description of the exclusion devices 100, 100' and an example balloon catheter 150, a method for delivering and deploying the exclusion device 100' to a left atrial appendage LAA will now be described. Referring back to FIG. 1, in an embodiment, a guidewire (not shown) is advanced after having been introduced into the vasculature via a percutaneous entry point, for example using the Seldinger technique, and tracked through the vasculature into a left atrium LA of a heart HE. Intravascular access to the right atrium RA may be achieved via a percutaneous access site to femoral venous access up to the inferior venal cava, or other known access routes. Thereafter, a guidewire is advanced through the circulatory system, eventually arriving at the heart HE. The guidewire is directed into the right atrium RA, traverses the right atrium and is made to traverse, with the aid of a transseptal needle or pre-existing hole, an atrial septum, thereby entering the left atrium LA. Once the guidewire is positioned, the endoluminal entry port and the atrial septum are dilated to permit entry of a guide catheter into the left atrium LA. Thereafter, the balloon catheter 150 is advanced over the guidewire and through a delivery shaft of the guide catheter into the left atrium LA through the punctured atrial septum and positioned proximate the left atrial appendage LAA. Although described as a transfemoral antegrade approach for percutaneously accessing left atrium LA, the balloon catheter 150 may be positioned within the desired area of the heart HE via different methods or routes. For example, and not by way of limitation, another possible path would be through the radial vein into the brachial vein, through the subclavian vein, through the superior vena cava into the right atrium, and then transseptally into the left atrium. Yet another possible path would be through the femoral artery into the aorta, through the aortic valve into the left ventricle, and then retrograde through the mitral valve into the left atrium. In another embodiment, the left ventricle LV may be accessed via a transapical approach, and the balloon catheter 150 may be advanced through the left ventricle LV, the mitral valve, and into the left atrium LA adjacent the left atrial appendage LAA. In addition, although described with the use of a guide catheter and a guidewire, in another embodiment hereof the delivery catheter 150 may access the left atrium LA without the use of a guidewire and/or a guide catheter.

Once the balloon catheter 150 is in place adjacent the left atrial appendage LAA, the balloon catheter 150 is advanced such that the first portion 110 of the occlusion device 100' is disposed adjacent the opening from the left atrium LA to the left atrial appendage LAA. Inflation fluid is then injected into the inflation lumen 158 to inflate the balloon 160 to radially expand the occlusion device 100' from the radially compressed configuration to the radially expanded configuration. The occlusion device 100' is inflated until the first portion 110 thereof spans the opening from the left atrium LA to the left atrial appendage LAA, as shown in FIG. 6. The inflation fluid may then be removed from the balloon 160 such that the balloon 160 deflates. The balloon catheter 150 may then be removed from the patient. As explained above, the second diameter D2 of the second portion 120 of the occlusion device 100 or 100' is preferably only large enough to enable the balloon catheter 150 to be removed. With the balloon catheter 150 removed, the occlusion device 100 or 100' remains in the left atrial appendage LAA, blocking clots from escaping the left atrial appendage LAA.

As described above, the occlusion device 100 or 100' is made from a biodegradable or bioerodible material such that the occlusion device 100/100' degrades/erodes over a period of time after it is implanted in the left atrial appendage LAA. During the time it takes for the occlusion device 100/100' to degrade/erode, endothelialization occurs such that tissue grows in and around the occlusion device 100/100' such that when the occlusion device 100/100' completely degrades/erodes, the tissue closes the opening from the left atrial appendage LAA to the left atrium to prevent clots from escaping the left atrial appendage LAA. The occlusion device 100/100' may include other features to assist in endothelialization (or for other purposes) such as, but not limited to, coverings, graft material, coatings, drugs, and other features known to those skilled in the art.

FIGS. 25-28 show similar embodiments of occlusion devices 500, 500' for use in occluding the left atrial appendage, which are also similar to the embodiments of FIGS. 2 and 3. Referring to FIGS. 25-26, the occlusion device 500 includes a first portion 510, a second portion 520, and a third portion 530. In the embodiment of FIGS. 25-26, the second portion 520 is disposed between the first portion 510 and the third portion 530, and connects the first portion 510 to the third portion 530. The first and third portions 510, 530 are formed of a plurality of longitudinal strips or fingers 512, 532 disposed around the longitudinal axis LA of the occlusion device 500. The second portion 520 may be a tube. The fingers 512 of the first portion 510 may be coupled to the second portion 520 by tabs 514 that are narrower than the fingers 512. In other embodiments, the fingers 512 may be directly attached to the second portion 520 such that the tabs 514 are not needed. Similarly, the fingers 532 of the third portion 530 may be coupled to the second portion 520 by tabs 534 that are narrower than the fingers 532. In other embodiments, the fingers 532 may be directly attached to the second portion 520 such that the tabs 534 are not needed. FIG. 25 shows the occlusion device 500 in a radially compressed configuration such that the first, second, and third portions 510, 520, and 530 have substantially the same diameter.

In embodiments, the occlusion device 500 may be delivered to the left atrial appendage LAA on a balloon catheter such as the balloon catheter 150 described above. When the balloon catheter 150 is at the desired location, the balloon 160 is inflated to radially expand the occlusion device 500 from the radially compressed configuration shown in FIG. 25 to the radially expanded configuration shown in FIG. 26. In such an embodiment, the balloon 160 will have a third portion similar to the first portion 161 of the balloon 160 as shown in FIG. 5. When the balloon is inflated, the fingers 512 of the first section 510 and the fingers 532 of the third section 530 bend at their respective connections to the second section 520 such that each finger 512, 532 rotates outwardly away from the longitudinal axis LA and towards the second section 520, as shown in FIG. 26. Such an expanded configuration deployed in the left atrial appendage LAA prevents clots from escaping the left atrial appendage LAA. The occlusion device 500 may include other features to assist in endothelialization (or for other purposes) such as, but not limited to, coverings, graft material, coatings, drugs, and other features known to those skilled in the art.

The occlusion device 500' shown in FIGS. 27-28 is similar to the occlusion device 500 except that the occlusion device 500' includes only the first portion 510 and the second portion 520. All other aspects of the occlusion device 500' are the same as the occlusion device 500 and therefore are not repeated herein.

In each of the occlusion devices 500, 500', it is desirable to make the second diameter D2 as small as possible. As described in more detail above, when delivering and deploying the occlusion device 500 or the occlusion device 500' using a balloon catheter, the second diameter D2 need only be large enough such that the balloon catheter may be withdrawn from the radially expanded occlusion device 500 or 500' after the balloon of the balloon catheter has been deflated.

The occlusion devices 500, 500' may be formed of plastically deformable materials such that the occlusion devices 500, 500' may be plastically deformable. Such devices may also be referred to as balloon or mechanically expandable. Further, the occlusion devices 500, 500' are biodegradable or bioerodible such that the occlusion devices degrade/erode over time after being deployed within the left atrial appendage LAA of a human heart HE. For example, and not by way of limitation, plastically deformable and biodegradable/bioerodible materials suitable for use for the occlusion devices 500, 500' include biodegradable metals or metal alloys such as alloys whose main component (largest amount by weight) is selected from the group consisting of magnesium, iron, zinc or tungsten. Other plastically deformable and biodegradable/bioerodible materials include biodegradable polymers such as, but not limited to, poly L-lactic acid (PLLA), poly lactic acid (PLA), polyglycolic acid (PGA), poly glycolide-co-L-lactide acid (PGLA), polydioxanone (PDO), poly glycolide-co-caprolactone (PGCL), and similar materials.

FIGS. 7-10 show schematically another embodiment of an occlusion device 200 in accordance with embodiments herein. Occlusion device 200 includes a plastically deformable braided mesh 202 with a first end 203 coupled to a first collar 204, and a second end 205 coupled to a second collar 206, as shown in FIG. 7. FIGS. 7-9 show the occlusion device 200 coupled to a catheter 250 for delivery and deployment to a left atrial appendage. As used herein, the term "braided mesh" means a wire or plurality of wires 207 that overlap to form a mesh-like device that includes the wire(s) 207 and small openings 208 disposed between the overlapped portions of the wire(s) 207. In the embodiment shown, it is desirable for the openings 208 to be relatively small to prevent clots from escaping the left atrial appendage LAA, while there is no requirement to permit or restrict fluid flow into or out of the left atrial appendage LAA.

The wire(s) 207 of the occlusion device 200 may be formed of plastically deformable materials such that the occlusion device 200 is plastically deformable. Such devices may also be referred to as balloon or mechanically expandable. Further, the wire(s) 207 of occlusion device 200 may be biodegradable or bioerodible such that the occlusion device 200 degrades/erodes over time after being deployed within the left atrial appendage LAA of a human heart HE. For example, and not by way of limitation, plastically deformable and biodegradable/bioerodible materials suitable for use for the occlusion device 200 include biodegradable metal or metal alloys such as alloys whose main component (largest amount by weight) is selected from the group consisting of magnesium, iron, zinc or tungsten. Other plastically deformable and biodegradable/bioerodible materials include biodegradable polymers such as, but not limited to, poly L-lactic acid (PLLA), poly lactic acid (PLA), polyglycolic acid (PGA), poly glycolide-co-L-lactide acid (PGLA), polydioxanone (PDO), poly glycolide-co-caprolactone (PGCL), and similar materials.

The exemplary catheter 250 shown in FIGS. 7-9 includes an inner shaft 252 defining a guidewire lumen 254. The catheter 250 may also include an outer shaft 256 slideably disposed over the inner shaft 252. A distal tip 260 is coupled to the inner shaft 260 and includes a tip lumen in communication with the guidewire lumen 254 of the inner shaft 252. In the embodiment shown, the first collar 204 is slideably disposed over the inner shaft 252 and the second collar 206 is fixedly attached to a distal portion of the inner shaft 252 distal of the first collar 204. In such an arrangement, the first collar 204 is slideable relative to the second collar 206.

In an embodiment shown in FIGS. 7-8, the outer shaft 256 is not coupled to the first collar 204. However, the outer shaft 256 is arranged such that a distal end 258 of the outer shaft 256 abuts a proximal end of the first collar 204. Therefore, when the catheter 250 with the occlusion device 200 has been delivered to the left atrial appendage LAA, as described above, the outer shaft 256 is pushed distally, which causes the first collar 204 to slide distally over the inner shaft 252 towards the second collar 206. With the distance between the first collar 204 and the second collar 206 reduced, as shown by comparing FIG. 7 to FIG. 8, the braided mesh 202 radially expands, as shown in FIG. 8. In other embodiments, rather than pushing the outer shaft 256 such that the first collar 204 moves towards the second collar 206, the outer shaft 256 may be held in place and the inner shaft 252 may be pulled proximally. The outer shaft 256 prevents the first collar 204 from moving proximally, which pulling the inner shaft 252 causes the inner shaft 252 and the second collar 206 attached thereto to move proximally relative to the first collar 204, thereby causing the braided mesh 202 to radially expand. Any combination of pushing the outer shaft 256 and pulling the inner shaft 252 may be used to bring the first and second collars 204 and 206 closer together to radially expand the braided mesh 202. In some embodiments, if there is sufficient resistance against the first collar 204 without the outer shaft 256 such that pulling the inner shaft 252 does not cause the first collar to move proximally, the outer shaft 256 can be eliminated such that pulling the inner shaft 252 causes the second collar 206 to move towards the first collar 204 to radially expand the braid mesh 202.

Because the braided mesh 202 is plastically deformable, the occlusion device 200 remains in the radially expanded configuration as the outer shaft 256 is withdrawn, as shown in FIG. 9. After the occlusion device is radially expanded, a proximal portion 253 of the inner shaft 252 may be detached from a distal portion 257 of the inner shaft 252 and removed from the patient, leaving the distal portion 257 of the inner shaft 252, the distal tip 260, and the occlusion device 200 in the radially expanded configuration at the treatment site. The proximal portion 253 of the inner shaft 252 may be detached from the distal portion 257 of the inner shaft 252 in various ways known to those skilled in the art, For example, and not by way of limitation, a weakened portion 255 of the inner shaft 252 may be disposed between the proximal portion 253 and the distal portion 257. After the occlusion device 200 is radially expanded, the weakened portion 255 may be broken, such as by an electrical charge or mechanical movement. In other embodiments, as shown in FIG. 12, a distal end of the proximal portion 253 of the inner shaft 252 may have an external thread 270 and a proximal end of the distal portion 257 of the inner shaft 252 may have an internal thread 272. After the occlusion device 200 is radially expanded, the proximal portion 253 of the inner shaft 252 is rotated to unscrew the proximal portion 253 from the distal portion 257. The threads may be reversed such that the distal portion 257 includes the external thread and the proximal portion including the internal thread. Other ways to connect and disconnect the proximal portion 253 from the distal portion 257 may be utilized, as would be apparent to those skilled in the art.

As with the embodiment described with respect to FIGS. 1-6, the catheter 250 with the occlusion device 200 coupled thereto may be advanced to the left atrium LA transseptally, transapically, or by other routes known to those skilled in the art. Once in place adjacent the left atrial appendage LAA, the catheter 250 is located such that upon expansion the widest portion of the braided mesh 202 will block the opening between the left atrium LA and the left atrial appendage LAA. Once the occlusion device 200 is radially expanded, the outer shaft 256, if used, may be withdrawn, the proximal portion 253 of the inner shaft 252 may be disconnected from the distal portion 257 of the inner shaft 252, and the proximal portion 253 withdrawn, as shown in FIGS. 9-10. This leaves the distal portion 257 of the inner shaft 252, the distal tip 260, and the occlusion device 200 in the radially expanded configuration blocking the left atrial appendage LAA, as shown in FIG. 11.

The embodiment of FIGS. 7-11 shows an inner shaft 252 with a guidewire lumen 254 to track the catheter 250 over a guidewire. However, the guidewire lumen 254 leaves a small opening when the occlusion device 200 is deployed in the left atrial appendage LAA. In some embodiments, the inner shaft 252 may act as a guidewire such that the guidewire lumen 254 is not needed. Such embodiments do not include the opening left by the guidewire lumen 254. In other embodiments with the guidewire lumen 254, the guidewire lumen 254 may be closed off after the catheter 250 has been tracked over the guidewire to the treatment site. For example, and not by way of limitation, the guidewire may be removed and a blocker may than be pushed into the guidewire lumen 254 to block the guidewire lumen 254 in the distal portion 257 of the inner shaft. The blocker may interact with a portion of the inner surface of the inner shaft 252 to lock the blocker in place. In other embodiments, when the proximal portion of the inner shaft is disconnected from the distal portion of the inner shaft, a blocker may be released to block the guidewire lumen. For example, and not by way of limitation, a flap or other blocker may be attached to an inner surface of the distal portion of the inner shaft. When the proximal portion of the inner shaft is disposed within the distal portion of the inner shaft, the flap is pressed against the inner surface of the distal portion. When the proximal portion of the inner shaft is removed, the flap is released to block the guidewire lumen. Other methods and devices to block the guidewire lumen after delivery of the catheter to the desired location may also be utilized.

FIGS. 13-19 show another embodiment of an occlusion device 300 according to embodiments disclosed herein. The occlusion device 300 of FIGS. 13-19 includes a plurality of longitudinal struts 302 disposed adjacent to each other in a generally cylindrical pattern with gaps 303 between circumferentially adjacent struts 302. When in the radially compressed configuration as shown in FIG. 13, the gaps 303 are small or closed due to adjacent struts 302 circumferentially abutting each other. The longitudinal struts 302 extend from a first collar 304 to a second collar 306. In the embodiment shown, the second collar 306 is also a distal tip of the catheter 350. The first and second ends of each of the struts are attached the first and second collars 304, 306, respectively. In some embodiments, the first and second collars 304/306 may be formed integrally with the struts 302. For example, and not by way of limitation, the combination of the first and second collars 304, 306 and the struts 302 may be cylindrical tube, and the gaps 303 may be cut into the cylindrical tube to form the struts 302. The cuts end distal of the proximal end and proximal of the distal end of the cylindrical tube, leaving the uncut portions of the cylindrical tube as the first and second collars 304, 306. The occlusion device 300 is delivered to and deployed at the treatment site using a catheter 350. In the present embodiment, the catheter 350 includes a shaft 352 including a guidewire lumen 354. Further details of the catheter 350 will be described with respect to devices and methods for deploying the occlusion device 300.

The struts 302 of the occlusion device 300 may be formed of plastically deformable materials such that the occlusion device 300 is plastically deformable. Such devices may also be referred to as balloon or mechanically expandable. Further, the struts 302 of the occlusion device 300 may be biodegradable or bioerodible such that the occlusion device 300 degrades/erodes over time after being deployed within the left atrial appendage LAA of a human heart HE. For example, and not by way of limitation, plastically deformable and biodegradable/bioerodible materials suitable for use for the occlusion device 300 include biodegradable metal or metal alloys such as alloys whose main component (largest amount by weight) is selected from the group consisting of magnesium, iron, zinc or tungsten. Other plastically deformable and biodegradable/bioerodible materials include biodegradable polymers such as, but not limited to, poly L-lactic acid (PLLA), poly lactic acid (PLA), polyglycolic acid (PGA), poly glycolide-co-L-lactide acid (PGLA), polydioxanone (PDO), poly glycolide-co-caprolactone (PGCL), and similar materials.

As shown in FIG. 14, the occlusion device 300 is radially expanded by moving the first and second collars 304, 306 closer to each other. As shown in FIGS. 1 and 2, the struts may include a defect or hinge 305 for preferential bending when the collars 304, 306 are moved closer to each other.

FIGS. 15 and 16 show an embodiment of a mechanism for moving the first and second collars 304, 306 closer to each other in order to radially expand the occlusion device 300. In the embodiment shown, the shaft 352 extends distally to the second collar/distal tip 306/360. A tip lumen of the second collar/distal tip 306/360 aligns with the guidewire lumen 354 of the inner shaft. However, the shaft 352 is not connected to the second collar/distal tip 306/360 such that the shaft 352 may move relative to the second collar/distal tip 306/360.

As shown in FIGS. 15 and 16, a portion of the shaft 352 includes threads 370 on an outer surface thereof. The first collar 304 includes mating threads 372 on an inner surface thereof. Therefore, as shown in FIG. 15, the threads 370 on the outer surface of the shaft 352 are mated with the threads 370 on the inner surface of the first collar 304. The catheter 350 with the occlusion device 300 attached thereto in the radially compressed configuration shown in FIG. 15 is delivered to the left atrial appendage LAA as described above. When it is desired to radially expand the occlusion device 300, the shaft 352 is rotated. The shaft 352 is prevented from retracting. Therefore, the first collar 304 moves distally along the threads 370, as shown in FIG. 16. By moving the first collar 304 closer to the second collar 306, the struts 302 must bend, and do so at the hinges 305. In an embodiment, when the first collar 304 reaches the distal end of the threads 370 of the shaft 352, the shaft 352 may be withdrawn proximally, leaving just the occlusion device 300 in the radially expanded configuration, as shown in FIG. 19.

As explained above, it is desirable to leave only small gaps or openings in the occlusion device 300 such that clots cannot escape the left atrial appendage LAA. As also explained above, if the shaft 352 is removed, an opening 309 in the first collar 304 that the shaft 352 extended through may be such an undesirable opening. Therefore, in an embodiment, as shown in FIGS. 17-18 flaps 380 may be attached to a distal or proximal end of the first collar 304. In the embodiment shown in FIGS. 17-18, the flaps 380 are attached to a distal end of the first collar 304. The flaps 380 are hingedly connected to the first collar 380. Thus, when the shaft 352 is disposed through the first collar 304 (not shown in FIG. 17 for clarity), the shaft 352 extends the flaps 380 such that they are generally longitudinally oriented relative to the catheter 350. When the shaft 352 is withdrawn from the opening 307, the flaps 380 fold towards the central longitudinal axis LA of the first collar 304, as shown in FIG. 18. The flaps 380 close the opening 309 or significantly reduce the size of the opening 309 to prevent clots from exiting the left atrial appendage LAA. The struts 302 are omitted from FIGS. 17 and 18 for clarity. Although FIGS. 17-18 show four flaps, this is not meant to be limiting, and more or fewer flaps may be utilized. The flaps 380 may be made from the same material as the first collar 304 and the struts 302, or from a different material.

As explained above with respect to the previous embodiments, the catheter 350 with the occlusion device 300 coupled thereto may be advanced to the left atrium LA transseptally, transapically, or by other routes known to those skilled in the art. Once in place adjacent the left atrial appendage LAA, the catheter 350 is located such that upon expansion the widest portion of the struts 302 will block the opening between the left atrium LA and the left atrial appendage LAA. Once the occlusion device 300 is radially expanded, the shaft 352 may be withdrawn, as shown in FIGS. 16 and 19. This leaves the distal portion occlusion device 300 in the radially expanded configuration blocking the left atrial appendage LAA, as also shown in FIG. 19.

The threaded shaft 352 described above with respect to the embodiment of FIGS. 15-19 may be used in the embodiment of FIGS. 7-11 instead of the deployment mechanisms described with respect to that embodiment. Further, the deployment mechanisms described with respect to the embodiment of FIGS. 7-12 may be used with the occlusion device 300 described with respect to FIGS. 13-19.

FIGS. 20-24 show another embodiment of an occlusion device 400 according to embodiments disclosed herein. The occlusion device 400 of FIGS. 20-24 is a shape memory wire 402 configured to occlude the left atrial appendage LAA. The wire 402 is delivered to the left atrial appendage in a catheter 404. When disposed in a lumen 406 of the catheter 404, the wire 402 is in a straightened configuration (the size of the lumen as compared to the wire 402 is exaggerated in the drawings for clarity). The catheter 404 with the wire 402 disposed therein with the wire 402 in the straightened configuration is delivered to the left atrial appendage LAA in one of the methods described above. When at the treatment site, the wire 402 is pushed out of an opening 408 at a distal end of the catheter 404. No longer restrained by the catheter, the wire 402 returns to its pre-set shape, as shown in FIG. 21. The wire 402 may be pushed out of the catheter 404 using a pusher 410, as shown in FIG. 21. In other embodiments, the wire 402 itself may be pushed, and then a proximal portion of the wire 402 to be removed may be separated from a distal portion of the wire 402 which has been deployed in the left atrial appendage LAA.

Once deployed, the wire 402 fills the left atrial appendage LAA, as shown in FIGS. 23-24, thereby preventing clots from escaping the left atrial appendage LAA. In the embodiment shown in FIGS. 21-23, the pre-set shape is a spiral. However, this is not meant to be limiting, and the wire 402 may be pre-set to other shapes to prevent clots from escaping the left atrial appendage LAA. For example, and not by way of limitation, FIG. 24 shows a pre-set shape that may be described as a coil similar to embolic coils or brain aneurysm coils. Other shapes may also be used provided that they sufficiently block the left atrial appendage LAA to prevent clots from exiting the left atrial appendage.

The wire 402 of the occlusion device 400 may be formed of shape memory material. Further, the wire 402 of the occlusion device 400 is biodegradable or bioerodible such that the occlusion device 400 degrades/erodes over time after being deployed within the left atrial appendage LAA of a human heart HE. For example, and not by way of limitation, shape memory and biodegradable/bioerodible materials suitable for use for as the wire 402 of the occlusion device 400 include biodegradable metal or metal alloys such as alloys whose main component (largest amount by weight) is selected from the group consisting of magnesium, iron, zinc or tungsten. Other shape memory and biodegradable/bioerodible materials include biodegradable polymers such as, but not limited to, poly L-lactic acid (PLLA), poly lactic acid (PLA), polyglycolic acid (PGA), poly glycolide-co-L-lactide acid (PGLA), polydioxanone (PDO), poly glycolide-co-caprolactone (PGCL), and similar materials.

While various embodiments according to the present invention have been described above, it should be understood that they have been presented by way of illustration and example only, and not limitation. Various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. An occlusion device for occluding a left atrial appendage, the occlusion device comprising:
    a first portion, the first portion comprising a plurality of fingers;
    a second portion attached to the first portion; and
    at least one of a covering, a graft material, a coating, or a drug for promoting endotheliazation when the occlusion device is implanted in a left atrial appendage,
    wherein the occlusion device is plastically deformable from a radially compressed configuration to a radially expanded configuration,
    wherein the radially compressed configuration, the plurality of fingers are disposed around a longitudinal axis of the occlusion device,
    wherein in the radially expanded configuration, the first portion has a larger cross-sectional profile than the second portion, wherein the plurality of fingers are unattached to each other except through the second portion, and
wherein the occlusion device is biodegradable.

2. The occlusion device of claim 1, wherein the occlusion device further includes a third portion, wherein the second portion is disposed between the first portion and the third portion, and wherein in the radially expanded configuration, the third portion has a larger cross-sectional profile than the second portion.

3. The occlusion device of claim 1, wherein the plurality of fingers of the first portion in the radially expanded configuration move radially outward and rotate towards the second portion.

4. The occlusion device of claim 1, wherein the occlusion device further includes a third portion, wherein the second portion is disposed between the first portion and the third portion, and wherein in the radially expanded configuration, the third portion has a larger cross-sectional profile than the second portion.

5. The occlusion device of claim 4, wherein the third portion comprises a plurality of fingers disposed around a longitudinal axis of the occlusion device in the radially compressed configuration.

6. The occlusion device of claim 5, wherein the plurality of fingers of the third portion in the radially expanded configuration move radially outward and rotate towards the second portion.

7. The occlusion device of claim 1, wherein the occlusion device is biodegradable over a period of time during which endotheliazation occurs such that tissue grows in and around the occlusion device and closes the opening from the left atrial appendage to the left atrium to prevent clots from escaping the left atrial appendage.

8. The occlusion device of claim 1, further comprising tabs coupling the plurality of fingers to the second portion, wherein the tabs are narrower than the fingers.

9. The occlusion device of claim 1, wherein the first portion is configured to attach the occlusion device to tissue at an opening between a left atrium and the left atrial appendage.

* * * * *